US010023517B2

(12) United States Patent
Verkuijl et al.

(10) Patent No.: US 10,023,517 B2
(45) Date of Patent: Jul. 17, 2018

(54) LACTYLATE PURIFICATION PROCESS

(71) Applicant: PURAC BIOCHEM BV, Gorinchem (NL)

(72) Inventors: Bastiaan Jeroen Victor Verkuijl, Gorinchem (NL); Andre Banier De Haan, Gorinchem (NL)

(73) Assignee: PURAC BIOCHEM BV, Gorinchem (NL)

( * ) Notice: Subject to any disclaimer, the term of this patent is extended or adjusted under 35 U.S.C. 154(b) by 0 days.

(21) Appl. No.: 15/537,698

(22) PCT Filed: Dec. 22, 2015

(86) PCT No.: PCT/EP2015/081087
§ 371 (c)(1),
(2) Date: Jun. 19, 2017

(87) PCT Pub. No.: WO2016/102625
PCT Pub. Date: Jun. 30, 2016

(65) Prior Publication Data
US 2017/0349525 A1    Dec. 7, 2017

(30) Foreign Application Priority Data

Dec. 22, 2014  (EP) .................................... 14199579

(51) Int. Cl.
*C07C 59/185*    (2006.01)
*C07C 51/48*     (2006.01)
(Continued)

(52) U.S. Cl.
CPC ............ *C07C 51/48* (2013.01); *C07C 53/126* (2013.01); *C07C 67/58* (2013.01); *C07C 69/24* (2013.01)

(58) Field of Classification Search
CPC ...................................................... C07C 51/48
(Continued)

(56) References Cited

U.S. PATENT DOCUMENTS

| 2,733,252 | A |   | 1/1956 | Thompson et al. |
| 2,789,992 | A | * | 4/1957 | Thompson ............. C07C 59/08 |
|           |   |   |        | 426/653 |

FOREIGN PATENT DOCUMENTS

| EP | 2 082 739 A1   | 7/2009 |
| WO | 2014/167069 A1 | 10/2014 |

OTHER PUBLICATIONS

Boutte et al., "Stearoyl-2-lactylates and oleoyl lactylates," Emulsifiers in Food Technology, 2004, pp. 206-225.
(Continued)

*Primary Examiner* — Deborah D Carr
(74) *Attorney, Agent, or Firm* — Oliff PLC (57) ABSTRACT

A method for separation of fatty acid from a mixture having fatty acid, the corresponding acyl lactylate and lactic acid, method having steps of: a) providing dispersion of mixture in polar carrier; b) adjusting dispersion mixture to pH from 5-9; and, c) extracting fatty acid from dispersion carrier mixture into solvent immiscible with polar carrier, obtaining fatty acid solution and aqueous raffinate having lactic acid and fatty acid lactylate. Polar carrier has from 70-100 wt. % of water and from 0-30 wt. % of one or more miscible, polar co-solvents. Aqueous raffinate may be further processed by: i) acidifying raffinate to pH from 0-3; and, either ii)a) allowing acidified raffinate to separate into two layers and separating lower, aqueous layer from residual layer of acyl lactylate, or ii)b) extracting fatty acid lactylate from acidified raffinate into second solvent which is immiscible with aqueous raffinate, obtaining an acyl lactylate solution.

15 Claims, 2 Drawing Sheets

(51) Int. Cl.
 C07C 67/58 (2006.01)
 C07C 53/126 (2006.01)
 C07C 69/24 (2006.01)
(58) Field of Classification Search
 USPC .......................................................... 554/122
 See application file for complete search history.

(56) References Cited

OTHER PUBLICATIONS

Osipow et al., "Fatty Acid Lactylates," D&CI, 1969.
Mar. 11, 2016 International Search Report issued in International Patent Application No. PCT/EP2015/081087.
Mar. 11, 2016 Written Opinion of the International Searching Authority issued in International Patent Application No. PCT/EP2015/081087.

* cited by examiner

LACTYLATE PURIFICATION PROCESS

FIELD OF THE INVENTION

The present invention relates to a process for the separation and purification of synthesized acyl lactylates, also known as fatty acid lactylates. More particularly, the present invention relates to a process for the independent separation and purification of acyl lactylate and the corresponding fatty acid from a mixture comprising said lactylate, said fatty acid and lactic acid, wherein said process comprises extraction with organic solvents.

BACKGROUND TO THE INVENTION

The term "acyl lactylate" refers to a compound having an acyl group from a fatty acid attached to one (monolactylates) or several lactic acid molecules (dilactylates and higher lactylates) and a proton (H⁺) or another cation attached to the terminal carboxylate. A representative acyl lactylate may possess the general structure:

RCO—(O—CHCH₃—CO)$_n$—OH wherein RCO is the acyl radical of a fatty acid, R typically having from 3 to 35 carbon atoms, and n is an integer of from 1 to 10. The hydrocarbon chain (R) can be linear or branched, may be saturated or unsaturated and may be substituted by one or more hydroxyl groups.

Such lactylates are common food additives: several types of lactylate can function as emulsifiers or humectants in food items such as baked goods, cereals, chewing gums and desserts. An example of such use is disclosed in Boutte et al. *Stearoyl-2-lactylates and oleoyl lactylates*, Pages 206-225, Emulsifiers in Food Technology, R. J. Whitehurst ed., Blackwell Publishing Ltd., Oxford, UK (2004).

Other lactylates find use as surfactants, viscosity modifiers, emulsifiers, foam boosters and stabilizers in personal care applications: acyl lactylates may serve to improve skin feel, skin softness and moisturization and reduce tackiness during a wet to dry transition after product application.

Osipow, et al., *Fatty Acid Lactylates*, pp. 1-12 (1969) describes the use of stearoyl lactylic acid and its sodium salt as a cosmetic gelling agent. Interestingly this citation also teaches that caproyl lactylate and sodium lauroyl lactylate are non-toxic and can exhibit anti-microbial activity. Developing this concept, EP 2 082 739 A1 (Purac Biochem BV) describes the use of lactylates for preventing or treating infections caused by gram-positive bacteria in animals.

To enjoy utility in regulated applications such as cosmetics and functional nutritional products, it will be evident that the acyl lactylates need to be of high purity. The present application is directed to the purification of synthesized acyl lactylates.

U.S. Pat. No. 2,733,252 (Thompson et al.) describes a process for the preparation of acyl lactylates in which lactic acid and a fatty acid are subjected to direct esterification at a temperature of from 100° C. to 250° C. in the presence of an alkali catalyst. U.S. Pat. No. 2,789,992 (Thompson et al.) describes a process for synthesizing acyl lactylates by reacting lactic acid with an acid chloride of fatty acid. WO2014/167069 (Purac Biochem BV) describes a process for the preparation of a salt of a fatty acid ester of inter alia lactic acid which comprises heating an oil, comprising a triglyceride fatty acid ester in admixture with a catalyst and a salt of lactic acid at a temperature at or above the melting temperature of the lactic acid and subjecting the mixture to ester interchange.

The reaction products obtained by the aforementioned processes usually contain a considerable amount of both lactic acid and fatty acid, derived from the starting materials, in addition to the desired fatty acid ester of lactic acid. Thus the end product of the reaction may be regarded as a mixture of the desired product acyl lactylate, higher order lactylates, lactic acid and free fatty acid or their salts. These species may be present in the mixture as salts, typically alkali metal, ammonium or amine salts.

The provision of such a mixture is obviously at odds with the commercial requirement for acyl lactylate products of higher purity. It is therefore an object of the present invention to provide a commercially feasible process whereby the components of these mixtures may be separated.

Problematically both fatty acid and acyl lactylate, possess the same long fatty acid chain which is strongly hydrophobic. It would therefore be expected that these products, and more particularly products having larger acyl groups, could not be separated by making use of a liquid-liquid extraction procedure: classical liquid-liquid extractions make use of the principle that the solubility of two compounds differ in two different phases which cannot be mixed together.

Furthermore, the mixture of fatty acid and acyl lactylates is known to have strong emulsifying properties. A skilled person would consider that these properties would render it difficult to separate the phases in the liquid-liquid extraction procedure.

STATEMENT OF THE INVENTION

In accordance with a first aspect of the present invention, there is provided a method for the separation of fatty acid from a mixture comprising fatty acid, the corresponding acyl lactylate and lactic acid, said method comprising the steps of:
a) providing a dispersion of said mixture in a polar carrier;
b) adjusting the dispersion mixture to a pH of from 5 to 9; and,
c) extracting the fatty acid from the dispersion carrier mixture into a solvent immiscible with said polar carrier, thereby obtaining a fatty acid solution,
   wherein said polar carrier comprises, by weight of said carrier, from 70 to 100 wt. % of water and from 0 to 30 wt. % of one or more miscible, polar co-solvents.

This method unexpectedly enables the use of a simple, liquid-liquid extraction procedure to remove fatty acid from a mixture which further comprises an acyl lactylate bearing the same hydrophobic acyl group.

The efficacy of step c) in extracting fatty acid from the initial mixture can be improved by performing step c) as multi-stage extraction. At the industrial or commercial scale, a counter-current multi-stage extraction is preferred.

Where necessary, the derived fatty acid solution can be further processed to recover the fatty acid therefrom. At least a portion and, optionally, all of any solvent removed from the fatty acid solution by distillation or the like can, advantageously, be recycled to the extraction step c). The fatty acid can itself be re-used as a reactant in the formation the corresponding acyl lactylate. This presents an important economic advantage in the production of acyl lactylates as the cost of fatty acid—which is driven by the prices of the raw materials of the acid—tends to be both high and volatile.

In accordance with a second aspect of the invention, there is provided a method for separating acyl lactylate from a mixture comprising said lactylate, the corresponding fatty acid and lactic acid, said method comprising the steps of:

a) providing a dispersion of said mixture in a polar carrier;
b) adjusting the dispersion mixture to a pH of from 5 to 9;
c) extracting the fatty acid from the dispersion carrier mixture into a first solvent which is immiscible with said polar carrier, thereby obtaining a fatty acid solution and an aqueous raffinate comprising lactic acid and fatty acid lactylate;
d) acidifying said raffinate to a pH of from 0 to 3; and,
e) allowing said acidified raffinate to separate into two layers and separating the lower, aqueous layer from the residual layer of acyl lactylate, wherein said polar carrier comprises, by weight of said carrier, from 70 to 100 wt. % of water and from 0 to 30 wt. % of one or more miscible, polar co-solvents.

As noted above, the efficacy of step c) in extracting fatty acid from the initial mixture can be improved by performing step c) as multi-stage extraction.

In accordance with a third aspect of the invention, there is provided a method for separating acyl lactylate from a mixture comprising said lactylate, the corresponding fatty acid and lactic acid, said method comprising the steps of:

a) providing a dispersion of said mixture in a polar carrier;
b) adjusting the dispersion mixture to a pH of from 5 to 9;
c) extracting the fatty acid from the dispersion carrier mixture into a first solvent immiscible with said polar carrier, thereby obtaining a fatty acid solution and an aqueous raffinate comprising lactic acid and fatty acid lactylate;
d) acidifying said raffinate to a pH of from 0 to 3; and,
f) extracting the fatty acid lactylate from the acidified raffinate into a second solvent which is immiscible with said aqueous raffinate, thereby obtaining an acyl lactylate solution, wherein said polar carrier comprises, by weight of said carrier, from 70 to 100 wt. % of water and from 0 to 30 wt. % of one or more miscible, polar co-solvents.

The first and second solvents employed in this third aspect of the invention may be the same or different but the former is preferred. Moreover, it is here preferred that at least one and optimally both of step c) and step f) is a multi-stage extraction. In the latter embodiment, the specific process for the multi-stage extraction may be independently selected for each of steps c) and f).

In each of the above aspects of the invention, it is preferable for the solvents which are to be immiscible with the polar carrier (step c)) and the aqueous raffinate (step f)) to have a boiling point of less than 120° C. at atmospheric pressure. This reduces the energetic costs of evaporating those solvents to respectively recover the fatty acid and acyl lactylate from solution. And solvents distilled from the respective solutions can be recycled to steps c) and f), as desired.

The present invention finds particular utility in the separation of saturated or unsaturated fatty acids having an acyl group of from 8 to 24 carbon atoms from the mixture and, where applicable, the subsequent separation of the corresponding acyl lactylates from a raffinate comprising said lactylate and lactic acid. The hydrocarbon chain of such fatty acids may be linear or branched and may be substituted by one or more hydroxyl groups.

By referring to saturated or unsaturated fatty acids—and the corresponding lactylates—as having an acyl group of from 8 to 24 carbon atom, no limitation is intended on the individual chain length and sub-ranges for the number of carbon atoms in said acyl group. For example, the acyl group may have a chain length with a lower limit of from 8, 10, or 12 carbon atoms to an upper limit of 24, 22, 20, 18, 16, 14 or 12 carbons atoms. Exemplary ranges include from 8 to 18 carbons atoms, 8 to 16 carbons atoms and 10 to 14 carbon atoms. Good results have been obtained with C8 to C18 fatty acids, in particular C12 to C14 fatty acids and, more particularly with C12, lauric acid.

For completeness, named examples of fatty acids include caprylic acid, capric acid, lauric acid, myristic acid, palmitic acid, stearic acid, oleic acid, linoleic acid, alpha linolenic acid, ricinoleic acid, petroselinic acid, arachidic acid and behenic acid.

The present invention is also directed to the separated and purified products obtained from the above-defined methods. In following the second and third aspects of the invention, starting from a mixture comprising, by weight of the mixture, from 10 to 40 wt. % of fatty acid, from 30 to 70 wt. % of the corresponding acyl lactylate and, from 10 to 30 wt. % lactic acid, fatty acid lactylates can be prepared with a purity of at least 90% and commonly at least 95%.

Definitions

The term "comprising" as used herein will be understood to mean that the list following is non-exhaustive and may or may not include any other additional suitable items, for example one or more further feature (s), component (s), ingredient (s) and/or substituent (s) as appropriate.

Without intention to limit the application of the doctrine of equivalents to the scope of the claims, each numerical value expressing temperature, pH and quantity of an ingredient as mentioned herein should at least be construed in light of the number of reported significant digits and by applying ordinary rounding techniques.

As used herein, the use of the terms "acyl lactylate", "fatty acid" and "lactic acid" includes the alkali metal, ammonium or amine salts thereof, unless specified otherwise. It is preferred for the relevant acid portions of the acyl lactylate, fatty acid and lactic acid to be at least partially neutralized and sodium ($Na^+$) and potassium ($K^+$) are the preferred cations in this regard. Salts may be present in the initially provided mixture. Alternatively or additionally, salts such as NaCl, KCl, $Na_2SO_4$ or $K_2SO_4$ may be added to the mixture in forming the dispersion (step a)).

Water, for use as a (co-)solvent or carrier herein, is intended to mean water of low solids content as would be understood by a person of ordinary skill in the art. The water may, for instance, be distilled water, demineralized water, deionized water, reverse osmosis water, boiler condensate water, or ultra-filtration water. Tap water may be tolerated in certain circumstances.

As used herein "solvents" are defined in accordance with the German Technical Rules for Dangerous Substances (TRGS) 610 as compounds with a boiling point below 200° C. at atmospheric pressure and which are used to dissolve other materials. The term "alcoholic solvent" encompasses such solvents which are any water-soluble mono-alcohols, diols or polyols that are liquids at 25° C. at atmospheric pressure.

As used herein, "immiscible" refers to two fluid materials that, when positioned in contact with one another, form an interface which possesses phases of differing compositions on each side of said interface. Without being limited thereby, the interfacial energy may typically be from 0.2 mN/m to 30 mN/m.

If an organic liquid product has a boiling point region, then the onset (the lowest temperature) of the boiling point range at atmospheric pressure is taken as the nominal boiling point. Where necessary any measurement of the initial boiling point for materials should be conducted in accordance with ASTM Standard Test Method D1078-95, or its most current version.

DETAILED DESCRIPTION OF THE INVENTION

The present invention is directed to the separation of fatty acid lactylate (acyl lactylate) from a mixture comprising said lactylate, the corresponding fatty acid and lactic acid; as mentioned above, this mixture is generally derived as the direct product of prior art processes for the preparation of acyl lactylates. The presence of higher order lactylates in such mixtures is common and is not deleterious to the present invention. Moreover, the present invention is applicable to mixtures which comprise a plurality of fatty acids and a plurality of corresponding acyl lactylates, enabling said acids and lactylates to be separated.

The mixtures as derived in U.S. Pat. Nos. 2,733,252 and 2,789,992 (both Thompson et al.) are lipoidal or pasteous: to drive each disclosed reaction to completion, elevated temperatures are employed with, where applicable, water being distilled off or hydrogen chloride being evolved.

An exemplary mixture derivable from the above mentioned art may be characterized by comprising, by weight of the mixture: from 10 to 40 wt. % of fatty acid; from 30 to 70 wt. % of the corresponding acyl lactylate; and, from 10 to 30 wt. % lactic acid.

Steps a) and b)

Steps a) to c) of the processes delineated above recite the separation of the constituent fatty acid(s) from the provided mixture.

The polar carrier employed in step a) comprises, by weight of the carrier, at least 70 wt. %, of water and from 0 to 30 wt. % of one or more miscible, polar co-solvents. In a preferred embodiment of the present invention, the polar carrier comprises at least 80 wt. %, preferably at least 90 wt. % and more preferably at least 95 wt. %, by weight of the carrier, of water. A polar carrier consisting only of water may also be useful.

When miscible co-solvents are included in the polar carrier, the polar ($\delta_p$) component of the Hansen Total Solubility Parameter ($\delta_t$) for each added co-solvent and/or the weighted average polar ($\delta_p$) component of the Hansen Total Solubility Parameter ($\delta_t$) for an added mixture of co-solvents should be ≥5 MPa$^{1/2}$ as determined at 25° C. at atmospheric pressure. The disclosure of *Hansen Solubility Parameters, A User's Handbook*, 2nd Edition, Charles M. Hansen, CRC Press (2007) is hereby incorporated by reference. Alternatively or additionally, the added miscible polar co-solvents should be characterized by a boiling point of 25° C. to 190° C. at atmospheric pressure.

Suitable miscible, polar co-solvents include but are not limited to: alcoholic solvents such as methanol, ethanol, isopropanol, 1,2-hexanediol, propylene glycol and glycerol; polyglycols such as polyethylene glycol; formamides such as formamide, n-methyl formamide, dimethylformamide, ethylammonium nitrate; glycerol esters such as glyceryl triacetate (triacetin), glyceryl tripropionate (tripropionin), and glyceryl tributyrate (tributyrin); ethylene carbonate; aniline; tetrahydrofuran (THF); acetone; acetonitrile; acetic acid; ethylenediamine; trimethyl phosphate; dimethyl sulfoxide; and, combinations thereof. It is envisaged that other polar solvents with a similar Hansen polarity component ($\delta_p$) to the aforementioned solvents would also be suitable.

According to the separation method of the invention, the mixture of acyl lactylate(s), the corresponding fatty acid(s) and lactic acid is first dispersed in the polar carrier, typically under stirring or agitation. The amount of the polar carrier per kilogram of raw mixture need only be sufficient to form a dispersion. Usually the amount will be from 0.5 to 100 liters and preferably from 5 to 15 liters of polar carrier per kg of the raw mixture: this ensures that the dispersion has a viscosity such that it may be easily pumped.

The pH of the dispersion formed is then adjusted to from 5 to 9, preferably from 5 to 8 or from 5 to 7, by the addition of acids and/or bases thereto. Suitable acids include mineral acids such as HCl and suitable bases include alkali metal hydroxides, carbonates and hydrogen carbonates, for instance NaOH. Further compounds suitable for adjusting the pH of the dispersion will be apparent to a person of ordinary skill in the art. For mixtures containing C10 or C12 to C14 acyl lactylates, in particular, the preferred final pH of the dispersion is from 5.5 to 6.5, for example 6.

Upon lowering the pH, the dispersion becomes cloudy.

Step c)

In step c), fatty acid present in the dispersion of step b) is extracted into immiscible solvent, thereby forming a fatty acid solution, as the extract, and an aqueous raffinate comprising lactic acid and fatty acid lactylate. The solvent or solvent mixture introduced in extraction step c) must be immiscible with the polar carrier and must be a solvent for fatty acids. The immiscible solvent should be capable of dissolving fatty acid in an amount of at least 5 wt. % and preferably at least 10 wt. % based on the weight of the solvent.

Examples of suitable immiscible solvents include, but are not limited to: pentane; hexane; heptane; cyclohexane; dichloromethane; 1,2-dichlorethane; trichloromethane; tetrachloromethane; ethyl acetate; butyl acetate; methyl ethyl ketone (MEK); methyl-isobutyl-ketone; diethyl ether; methyl-t-butyl ether; di-iso-propyl ether; aromatics such as benzene, toluene, o-xylene, p-xylene, chlorobenzene and nitrobenzene; and, combinations thereof. Petroleum ether might be mentioned as an exemplary combination of such immiscible solvents. It is preferred that the solvent or solvent mixture has a boiling point of less than 120° C. at atmospheric pressure. And good results, in particular, have been obtained where the immiscible solvent is selected from dichloromethane; pentane; hexane; and, combinations thereof.

The immiscible solvent and the polar carrier are brought into contact in a suitable extractor, typically under mixing or turbulence, in order to allow mass transfer between the two liquids. As is known in the art, the amounts of any liquids added and removed from the extractor may be monitored volumetrically or by weight. By volume, the contacted amount of immiscible solvent and of the polar carrier will usually be equal. After contacting, the phases are allowed to coalesce and separate: the aqueous raffinate, containing the acyl lactylate and the lactic acid, is then split from the extract of the fatty acid dissolved in the immiscible solvent.

The purpose of step c) is to maximise partitioning of the fatty acids in the extract. More particularly, the aim is to maximize the fatty acid (FA) distribution coefficient, defined as $[FA]_{Extract}/[FA]_{Raffinate}$. The pH of the dispersion mixture aside, it will be recognized that the choice of co-solvent in the polar carrier, the choice of immiscible solvent, the temperature of extraction and the residence time in the extractor may be result effective variables in maximizing $D_{FA}$ for a given fatty acid: these may be adapted by a person of ordinary skill in the art. To reduce energetic costs, the extraction procedure c) should usually be conducted at a temperature of from 20 to 40° C.

The above paragraph aside, it will be recognized that a single extraction procedure—that is a single step c)—may not, in all circumstances, be sufficient to produce the desired separation of fatty acids from the acyl lactylates.

In an embodiment of the invention therefore, the acyl lactylate raffinate may be further purified by repeating the preceding dispersion and organic solvent extraction steps. More particularly, the raffinate may be re-dispersed in water (a)), the pH of the dispersion adjusted to from 5 to 9 (b)) and brought into contact with an immiscible solvent (c)), which solvent may be the same or different to that previously employed. The raffinate of that extraction step should thereby contain less contaminating free fatty acid, which has again passed into the extract for drawing or siphoning off. Where the level of free fatty acid within the raffinate is still considered to be too high, the steps may be further repeated.

Alternatively, step c) may be constituted by a multi-stage extraction. More particularly, multiple extraction procedures such as countercurrent distribution (CCD), thin-layer counter-current distribution, enhanced gravity counter-current distribution, partition column chromatography, counter-current chromatography, centrifugal liquid-liquid extractors, multi-stage cross-current extractors and counter-current extractors may be utilized. Instructive disclosures in this regard include: Walter et al. *The Theory and Practice of Cross-current and Counter-current Extraction in Liquid Extraction*, R. Treybal Ed. McGraw Hill, 1963; and, Schweitzer, P.A. *Handbook of Separation Techniques for Chemical Engineers*, Third Edition, McGraw-Hill, 1997.

The extract containing the fatty acid(s) dissolved in the immiscible solvent may then be further processed to separate the fatty acid(s). In certain embodiments, the immiscible solvent may simply be distilled from the solution, under suitable temperature and pressure conditions, and optionally recycled. Alternatively, the solution may be subjected to one or more cycles of heating to concentrate the solution by evaporation of a portion of the solvent, followed by cooling to precipitate fatty acid. This latter technique may be appropriate, for instance, where the acyl group of the fatty acid is unsaturated—as cis-trans conversions may be obviated—or where it is also desired to separate saturated, mono-unsaturated and di-unsaturated fatty acids from the solution. The table appearing in Kirk-Othmer, *Encyclopedia of Chemical Technology*, $3^{rd}$ Edition, Vol. 4, Page 827 (1978) may be instructive here as it shows the difference in solubility of various fatty acids at different temperatures in toluene and n-heptane.

The obtained fatty acid(s) may be recycled to the synthesis of the acyl lactylate.

Step d)

The separated aqueous phase or raffinate comprising the acyl lactylate in the polar carrier is acidified using an solution of sulphuric acid, phosphoric acid or, preferably, hydrochloric acid. This acidification is performed to obtain a pH of from 0 to 3, preferably from 0.5 or 1.5: it will typically be performed at a temperature of from 10° C. to 90° C., preferably from 20° C. to 60° C.

The concentration and amount of the acid must be sufficient to convert the acyl lactylate into its free acid form but should be below that which could result in charring or decomposition of the normal reaction equilibrium products. Typically, the aqueous hydrochloric, sulphuric or phosphoric acids will contain from 10 to 40 wt. % of the respective acid.

Step e)

In a first alternative embodiment, the resulting acidified mixture of step d) may simply be allowed to separate into two layers. The lower or aqueous layer (extract) may be drawn or siphoned off leaving the residual layer of acyl lactylate. That acyl lactylate may then be washed, for example, by stirring in a weak, 1 to 8 wt. % aqueous solution of sodium sulfate, followed by settling and drawing off and discarding the wash solution, and repeating with a fresh solution if desired. Alternatively, a weak, 0.05 to 0.1 wt. % solution of sulphuric acid can be used for washing.

Step f)

In an alternative embodiment, the resulting acidified reaction mixture of step d) is subjected to an extraction step by bringing said mixture into contact—in a suitable extractor and typically under mixing or agitation—with a solvent which is immiscible with the aqueous raffinate (i.e. water) and in which the free acid form of the acyl lactylate is soluble. This solvent may be the same or different to that employed in the or each extraction step c). The immiscible solvent should be capable of dissolving the acyl lactylate in an amount of at least 5 wt. % and preferably at least 10 wt. % based on the weight of the solvent.

Examples of suitable immiscible solvents include, but are not limited to: pentane; hexane; heptane; cyclohexane; dichloromethane; 1,2-dichlorethane; trichloromethane; tetrachloromethane; petroleum ether; ethyl acetate; butyl acetate; methyl ethyl ketone (MEK); methyl-isobutyl-ketone; diethyl ether; methyl-t-butyl ether; di-iso-propyl ether; aromatics such as benzene, toluene, o-xylene, p-xylene, chlorobenzene and nitrobenzene; and, combinations thereof. Petroleum ether might be mentioned as an exemplary combination of such immiscible solvents. It is again preferred that the solvent or solvent mixture has a boiling point of less than 120° C. at atmospheric pressure.

As previously noted, the amounts of the acidified raffinate and the immiscible solvent added and removed from the extractor may be monitored volumetrically or by weight and appropriately adjusted by the skilled practitioner. After contacting, the aqueous and organic phases are allowed to coalesce and separate: the aqueous raffinate, containing lactic acid, is then split from the extract of the acyl lactylate dissolved in the immiscible solvent. To obtain the acyl lactylate, the immiscible solvent may simply be distilled off from the solution, under suitable temperature and pressure conditions. Alternatively, the solution may be subjected to one or more cycles of heating to concentrate the solution by evaporation of a portion of the solvent followed by cooling to precipitate the acyl lactylate.

The present invention does not preclude the extraction step f) being a multi-stage extraction. Moreover, the obtained acyl lactylate can be further purified by other methods including, but not limited to, washing, recrystallization, filtration, suction or extraction.

Exemplary Embodiment of the Invention

A particularly preferred embodiment of the present invention entails the separation of one or more C12-C14 acyl lactylates from a mixture comprising said lactylate(s), the corresponding C12-C14 fatty acid(s) and lactic acid, said separation method comprising the steps of:

a) providing a dispersion of said mixture in a polar carrier;
b) adjusting the dispersion mixture to a pH of from 5 to 7;
c) extracting the fatty acid from the dispersion carrier mixture into a first solvent immiscible with said polar carrier, thereby obtaining a fatty acid solution and an aqueous raffinate comprising lactic acid and fatty acid lactylate;

d) acidifying said raffinate to a pH of from 0.5 to 1.5 using a solution of sulphuric acid, phosphoric acid or, preferably hydrochloric acid;

f) extracting the fatty acid lactylate from the acidified raffinate into a second solvent which is immiscible with said aqueous raffinate, thereby obtaining an acyl lactylate solution; and, g) distilling said acyl lacytlate solution to recover said acyl lactylate and recycling at least a portion of said second solvent distilled from said acyl lactylate solution to step f), wherein in said method:

said polar carrier comprises, by weight of said carrier, from 80 to 100 wt. % of water and from 0 to 20 wt. % of one or more miscible, polar co-solvents;

said first solvent and said second solvent are the same or different but each has a boiling point of less than 120° C. at atmospheric pressure; and, at least one of steps c) and f) comprises a multi-stage, counter-current extraction.

Figure 1:
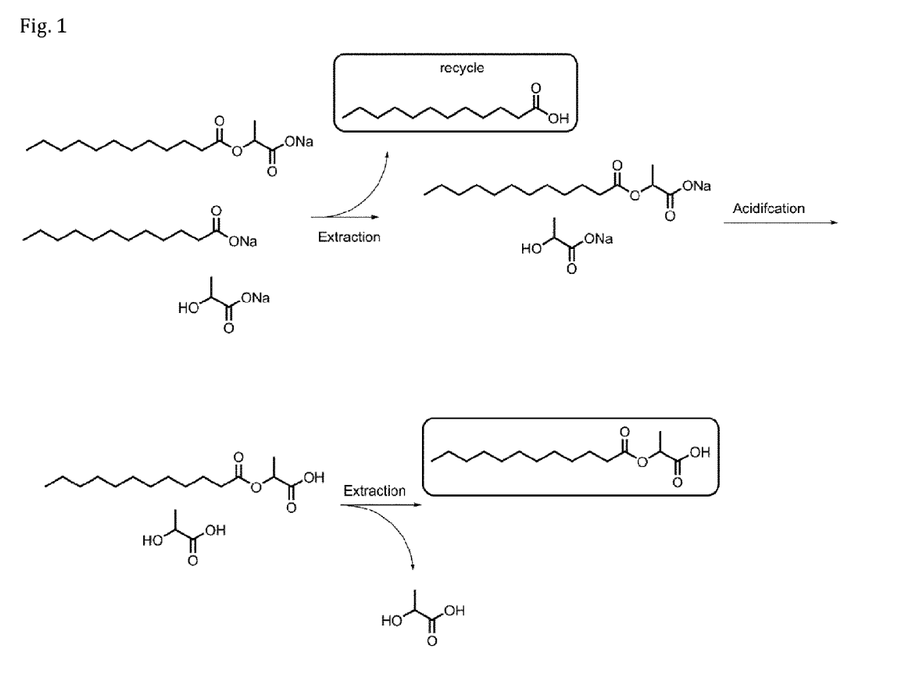
FIG. 1 illustrates an embodiment of the present invention in which lauric acid is separated from an initial mixture which further comprises sodium lauroyl lactylate and higher order lactylates, sodium laurate and lactic acid salts.
Figure 2:
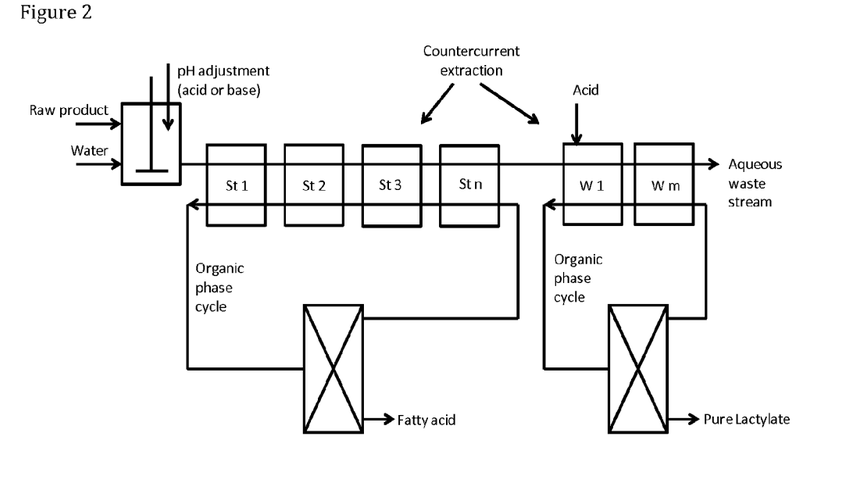
FIG. 2 illustrates an embodiment of the present invention in which a multi-stage, counter current extraction process is employed.

FIG. 2 appended hereto illustrates a process in accordance with a preferred embodiment of the invention wherein both extraction steps (c) and f)) are performed and are independently constituted by multi-stage counter-current extraction schemes. Such a process may, advantageously, be easily operable at a commercial or industrial scale.

Process step c) of the present invention is depicted as n-stages (St1, St2, St3 ... Stn) in which the organic solvent, immiscible with the polar carrier—here water—enters that stage (Stn) or the end of the extractor farthest from the feed point (St1) of the acidified aqueous dispersion: the aqueous and organic phases then pass counter-current to each other. The objective is to strip the fatty acid(s) from the aqueous feed dispersion into the organic phase.

The aqueous raffinate emerging from the nth stage is acidified and enters an m-stage (W1 ... Wm) counter-current extraction process, performed thereon using an organic solvent immiscible with said raffinate and which enters the extractor at stage Wm. The aqueous and organic phases again run counter-current to each other with acyl lactylate being stripped from the acidified aqueous raffinate into the organic phase.

Depending on the desired purity and yield of the final product: n will typically be from 1 to 20 and more usually from 3 to 10; and, m will typically be from 1 to 10 and more usually be from 2 to 5. Each box (St1-n; W1-m) of FIG. 2 may be independently be constituted by a device selected from: a mixer; a settler; a columnal contactor; a centrifugal contactor such as a CINC contactor; and, a Podbielniak contactor.

The fatty acid extract removed in the organic phase cycle of stages St1-n is subjected to distillation whereby the obtained immiscible solvent is recycled to stage n (Stn). Analogously, the acyl lactylate is here subjected to a distillation enabling the separated solvent to be recycled to stage W1-m.

The present invention will be further illustrated by the following Examples, without being limited thereto or thereby.

EXAMPLES

Example 1

Synthesis of Sodium Lauroyl Lactylate (SLL)

Lactic acid (88%; 80 g) and lauric acid (140 g) are put into a reaction vessel fitted with a distillation setup. NaOH (50%; 55 g) is added dropwise and the temperature is increased to reflux conditions. Water is distilled off and the temperature is increased to 190° C. When the acid value is around 70 mg KOH/g, the reaction is allowed to cool to room temperature, yielding an off-white paste (210 g).

The yielded material (hereinafter SSL) is a mixture of the sodium lauroyl lactylate (42%) together with higher order lactylates (5%) and the starting materials of the synthesis, sodium laurate (33%) and lactic acid salts (18%).

Example 2

Sodium Lauroyl Lactylate Purification

Two stock solutions were prepared. Firstly, SLL prepared according to Example 1 was dispersed in water (100 mg/10 mL), the resultant dispersion having a pH of 6.5. Secondly, to provide an internal standard, methyl laurate (ML) was dissolved in dichloromethane (dcm) (100 mg/10 mL).

The SLL stock solution was stirred up with heptane in equivolumous amounts (2/2 mL). After stirring for 30 minutes, the layers were allowed to settle and were separated. The organic layer was evaporated in vacuo and a product with predominantly fatty acid was retrieved.

The water layer was acidified with 0.5 mL 1N HCl(aq) to a pH of 1.0, after which precipitation occurred. This suspension was extracted with the ML/dcm stock solution and the resulting solution was subjected to Gas Chromatography analysis.

Analysis revealed that the final product contained 95 wt. % of lactylates, based on the free acid form. The main impurity was fatty acid (4%, GC area percentage).

Example 3

Sodium Lauroyl Lactylate Purification

Three stock solutions were prepared by dispersing three samples of SLL prepared according to Example 1 in water (100 mg/10 mL) under shaking. The pH of the resultant dispersions were adjusted to 6.5, 5.8 and 5.8 respectively using lactic acid or sodium hydroxide, as recorded in Table 1 below.

The three SLL stocks solution were independently stirred up with heptane in equivolumous amounts (2/2 mL). After stirring for 30 minutes, the layers were allowed to settle and were separated. A small amount of sodium chloride was added to each sample and each sample was then centrifuged for 1 hour at 8000 rpm—using a Beckman Coulter Avanti JE Centrifuge—to facilitate the phase separation. The organic layer of each of the three samples was evaporated in vacuo and products with predominantly fatty acid were retrieved and subjected to Gas Chromatography analysis. The purity of the recovered fatty acid is reported in Table 1 below based on the definition 100*(wt. % fatty acid)/(wt. % fatty acid+ wt. % lactylate), wherein the wt. % lactylate is based on the free acid form.

Each water layer from the three samples was acidified with 1N HCl (aq) to the pH values shown in Table 1 below, after which precipitation occurred. These suspensions were contacted at a 1:1 volume ratio with dichloromethane and stirred from 30 minutes at room temperature before being allowed to settle and separate. The dichloromethane layer of each sample was subjected to Gas Chromatography analysis. The purity of the recovered lactylate is reported in Table 1 below based on the definition 100*(wt. % lactylate)/(wt. % fatty acid+wt. % lactylate), wherein the wt. % lactylate is based on the free acid form.

The results of the analyses are given in Table 1 hereinbelow. The main impurity in the extracted lactylate, where applicable, was fatty acid.

TABLE 1

| Sample | Starting Lactylate | pH of Aqueous Dispersion | pH after Acidification | Fatty Acid Purity (from heptane layer) | Lactylate Purity (from dcm layer) |
|---|---|---|---|---|---|
| a | C12, SLL | 6.5 | 1.1 | 83.4 | 100.0 |
| b | C12, SLL | 5.8 | 1.1 | 82.1 | 100.0 |
| c | C12, SLL | 5.8 | 3.1 | 82.1 | 92.6 |

Example 4

Large Scale Extraction of Sodium Lauroyl Lactylate

Lactic acid (88%, 14.0 kg) was loaded into a reactor. After this, NaOH (4.4 kg) and lauric acid (approximately 11.5 kg) were added. The reaction mixture was heated stepwise to 190° C. and meanwhile water was distilled off. After the reaction proceeded sufficiently, the mixture was allowed to cool to room temperature and collected as an off-white solid (22 kg).

2.5 kg of the sodium lauroyl lactylate/fatty acid mixture was loaded into a reaction vessel. Water (30 L) and petroleum-ether 50-70 (25 L) were added. The mixture was stirred mechanically and a dispersion was formed. The pH of the dispersion was measured at 5.9. 50% NaOH (aq, 60 g) was added and the pH was measured at 6.3. The dispersion was stirred for 1 hour and allowed to settle until two layers were formed. The layers were separated and the organic layer was evaporated for recycling purposes.

The aqueous layer was subjected to a fourfold iterative process of pH adjustment and extraction. After this, a batch of petroleum ether (25 kg) was added to the aqueous layer. The mixture was stirred and 37% HCl (aq, 1 L) was added to attain a pH of 1.0. The dispersion was stirred for 1 hour and allowed to settle until two layers were formed. The top layer was collected and evaporated to dryness, yielding the lactylate as a yellow oil. Gas chromatography revealed this oil to have 94% purity.

Example 5

Sodium Caproyl Lactylate Purification

Sodium caproyl lactylate was provided as a mixture of the sodium caproyl lactylate (<50 wt. %) together with higher order lactylates and the starting materials of the synthesis, sodium caprylate and lactic acid salts.

Two stock solutions were prepared by independently dispersing 100 mg of the SCL in 10 mL of water. The pH of the resultant dispersions were adjusted to 4.8 and 6.6 respectively using lactic acid or sodium hydroxide, as recorded in Table 2 below.

The two SCL stocks solution were independently stirred up with heptane in equivolumous amounts (2/2 mL). After stirring for 30 minutes, the layers were allowed to settle and were separated. The organic layer of each of the two samples was evaporated in vacuo and products with predominantly fatty acid were retrieved and subjected to Gas Chromatography analysis.

Each water layer from the two samples was acidified with 1N HCl(aq) to the pH values shown in Table 2 below, after which precipitation occurred. These suspensions were contacted at a 1:1 volume ratio with dichloromethane and stirred from 30 minutes at room temperature before being allowed to settle and separate. The dichloromethane layer of each sample was subjected to Gas Chromatography analysis.

The results of the analyses are given in Table 2 hereinbelow. The main impurity in the extracted lactylate, where applicable, was fatty acid.

TABLE 2

| Sample | Starting Lactylate | pH of Aqueous Dispersion | pH after Acidification | Fatty Acid Purity (from heptane layer) | Lactylate Purity (from dcm layer) |
|---|---|---|---|---|---|
| d | C8, SCL | 4.8 | 1.1 | 93.5 | 89.4 |
| e | C8, SCL | 6.6 | 1.0 | 74.7 | 53.7 |

Example 6

Sodium Palmitoyl Lactylate Purification

Sodium palmitoyl lactylate (SPL) was provided as a mixture of the sodium palmitoyl lactylate (<50 wt. %) together with higher order lactylates and the starting materials of the synthesis, sodium palmitate and lactic acid salts.

Two stock solutions were prepared by independently dispersing two samples of SPL as provided in water (100 mg/10 mL) under shaking. The pH of the resultant dispersions were adjusted to 7.5 and 6.5 respectively using lactic acid or sodium hydroxide, as recorded in Table 3 below.

The two SPL stocks solution were independently stirred up with heptane in equivolumous amounts (2/2 mL). After stirring for 30 minutes, the layers were allowed to settle and were separated. A small amount of sodium chloride was added to each sample and each sample was then centrifuged for 1 hour at 8000 rpm—using a Beckman Coulter Avanti JE Centrifuge—to facilitate the phase separation. The organic layer of each of the two samples was evaporated in vacuo and products with predominantly fatty acid were retrieved and subjected to Gas Chromatography analysis.

Each water layer from the two samples was acidified with 1N HCl (aq) to the pH values shown in Table 3 below, after which precipitation occurred. These suspensions were contacted at a 1:1 volume ratio with dichloromethane and stirred from 30 minutes at room temperature before being allowed to settle and separate. The dichloromethane layer of each sample was subjected to Gas Chromatography analysis.

The results of the analyses are given in Table 3 hereinbelow. The main impurity in the extracted lactylate, where applicable, was fatty acid.

TABLE 3

| Sample | Starting Lactylate | pH of Aqueous Dispersion | pH after Acidification | Fatty Acid Purity (from heptane layer) | Lactylate Purity (from dcm layer) |
|---|---|---|---|---|---|
| f | C16, SPL | 7.5 | 1.0 | 86.6 | 71.0 |
| g | C16, SPL | 6.5 | 1.0 | 86.6 | 85.6 |

It will be apparent to those skilled in the art, upon consideration of the specification, that various modifications can be made in the disclosed embodiments without departing from the scope of the invention. It is therefore intended that the embodiments and examples be considered illustrative only, with the true scope of the invention being indicated by the following claims.

The invention claimed is:

1. A method for separation of fatty acid from a mixture comprising fatty acid, the corresponding acyl lactylate and lactic acid, said method comprising the steps of:
   a) providing a dispersion of said mixture in a polar carrier;
   b) adjusting the dispersion mixture to a pH of from 5 to 9; and,
   c) extracting the fatty acid from the dispersion carrier mixture into a solvent immiscible with said polar carrier, thereby obtaining a fatty acid solution,
   wherein said polar carrier comprises, by weight of said carrier, from 70 to 100 wt. % of water and from 0 to 30 wt. % of one or more miscible, polar co-solvents.

2. The method according to claim 1, wherein the immiscible solvent has a boiling point less than 120° C. at atmospheric pressure.

3. The method according to claim 1, wherein the immiscible solvent should be capable of dissolving said fatty acid in an amount of at least 5 wt. % based on the weight of the solvent.

4. The method according to claim 1, wherein at least a portion of the immiscible solvent is distilled from said fatty acid solution and recycled to extraction step c).

5. The method according to claim 1, wherein step c) is a multi-stage extraction.

6. A method for separating acyl lactylate from a mixture comprising said lactylate, the corresponding fatty acid and lactic acid, said method comprising the steps of:
   a) providing a dispersion of said mixture in a polar carrier;
   b) adjusting the dispersion mixture to a pH of from 5 to 9;
   c) extracting the fatty acid from the dispersion carrier mixture into a first solvent which is immiscible with said polar carrier, thereby obtaining a fatty acid solution and an aqueous raffinate comprising lactic acid and fatty acid lactylate;
   d) acidifying said raffinate to a pH of from 0 to 3; and,
   e) allowing said acidified raffinate to separate into two layers and separating the lower, aqueous layer from the residual layer of acyl lactylate
   wherein said polar carrier comprises, by weight of said carrier, from 70 to 100 wt. % of water and from 0 to 30 wt. % of one or more miscible, polar co-solvents.

7. A method for separating acyl lactylate from a mixture comprising said lactylate, the corresponding fatty acid and lactic acid, said method comprising the steps of:
   a) providing a dispersion of said mixture in a polar carrier;
   b) adjusting the dispersion mixture to a pH of from 5 to 9;
   c) extracting the fatty acid from the dispersion carrier mixture into a first solvent immiscible with said polar carrier, thereby obtaining a fatty acid solution and an aqueous raffinate comprising lactic acid and fatty acid lactylate;
   d) acidifying said raffinate to a pH of from 0 to 3; and,
   f) extracting the fatty acid lactylate from the acidified raffinate into a second solvent which is immiscible with said aqueous raffinate, thereby obtaining an acyl lactylate solution,
   wherein said polar carrier comprises, by weight of said carrier, from 70 to 100 wt. % of water and from 0 to 30 wt. % of one or more miscible, polar co-solvents.

8. The method according to claim 6, wherein said first solvent has a boiling point of less than 120° C. at atmospheric pressure.

9. The method according to claim 6, wherein at least a portion of said first solvent is distilled from the said fatty acid solution and recycled to extraction step c).

10. The method according to claim 7, wherein said second solvent has a boiling point of less than 120° C. at atmospheric pressure.

11. The method according to claim 7, wherein the first and second solvents are the same.

12. The method according to claim 7, wherein at least a portion of said second solvent is distilled from the acyl lactylate solution and recycled to step f).

13. The method according to claim 7, wherein at least one of step c) and step f) is a multi-stage extraction.

14. The method according to claim 1, wherein the fatty acid chain of the acyl lactylate has an acyl group with 8-18 carbon atoms.

15. The method according to claim 1, wherein said polar carrier comprises, by weight of said carrier:
   from 80 to 100 wt. % of water; and,
   from 0 to 20 wt. % of one or more miscible, polar co-solvents.

* * * * *